United States Patent
Nock et al.

(10) Patent No.: US 11,207,059 B2
(45) Date of Patent: Dec. 28, 2021

(54) BIOPSY IMAGING ROD WITH AN EGRESS PORT, WITH A BIOPSY MARKER AND WITH A BIASED PUSHROD

(71) Applicant: Devicor Medical Products, Inc., Cincinnati, OH (US)

(72) Inventors: Andrew Nock, Dayton, OH (US); Robert Householder, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 581 days.

(21) Appl. No.: 15/748,300

(22) PCT Filed: Jul. 27, 2016

(86) PCT No.: PCT/US2016/044285
§ 371 (c)(1),
(2) Date: Jan. 29, 2018

(87) PCT Pub. No.: WO2017/019780
PCT Pub. Date: Feb. 2, 2017

(65) Prior Publication Data
US 2018/0221000 A1 Aug. 9, 2018

Related U.S. Application Data

(60) Provisional application No. 62/198,491, filed on Jul. 29, 2015.

(51) Int. Cl.
*A61B 10/02* (2006.01)
*A61B 90/00* (2016.01)
*A61B 17/00* (2006.01)

(52) U.S. Cl.
CPC ........ *A61B 10/0233* (2013.01); *A61B 90/39* (2016.02); *A61B 2017/00004* (2013.01);
(Continued)

(58) Field of Classification Search
CPC ...... A61B 10/0233; A61B 2017/00004; A61B 2090/3908; A61B 2090/3925;
(Continued)

(56) References Cited

U.S. PATENT DOCUMENTS 5,526,822 A 6/1996 Burbank et al.
5,928,164 A 7/1999 Burbank et al.
(Continued)

OTHER PUBLICATIONS

C. R. Bard, Inc., Bard Biopsy, "Breast Tissue Markers Product Index," downloaded Dec. 26, 2016, from http://www.bardbiopsy.com/products/index_markers.php, 3 pgs.
(Continued)

*Primary Examiner* — Joanne M Hoffman
*Assistant Examiner* — Alexei Bykhovski
(74) *Attorney, Agent, or Firm* — Frost Brown Todd LLC (57) ABSTRACT

A biopsy imaging rod (100) includes an elongated rod member (200) having a sharp distal end (210) and a channel extending from a proximal end to an egress port (220) near the distal end, and it also includes an onboard biopsy marker (400) positioned in the channel proximal to the egress port. The biopsy imaging rod also includes a pushrod (300) slideably positioned in the channel adjacent to the biopsy marker extending from the proximal end of the elongated rod member to the egress port, the pushrod biased to bend toward the biopsy marker. The biopsy imaging rod may additionally include an imageable portion between the distal end and the egress port. Methods for making and using the biopsy imaging rod are also disclosed.

18 Claims, 6 Drawing Sheets

(52) U.S. Cl.
CPC .................. *A61B 2090/3908* (2016.02); *A61B 2090/3925* (2016.02); *A61B 2090/3954* (2016.02); *A61B 2090/3987* (2016.02)

(58) Field of Classification Search
CPC .... A61B 2090/3954; A61B 2090/3987; A61B 90/39; A61B 10/0275; A61B 2010/0208; A61B 2090/3904
See application file for complete search history.

(56) References Cited

U.S. PATENT DOCUMENTS

| | | | |
|---|---|---|---|
| 6,017,316 | A | 1/2000 | Ritchart et al. |
| 6,086,544 | A | 4/2000 | Hibner et al. |
| 6,066,122 | A | 5/2000 | Fisher |
| 6,162,187 | A | 12/2000 | Buzzard et al. |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 7,442,171 | B2 | 10/2008 | Stephens et al. |
| 7,507,210 | B2 | 3/2009 | Hibner et al. |
| 7,648,466 | B2 | 1/2010 | Stephens et al. |
| 7,831,290 | B2 | 11/2010 | Hughes et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 7,996,065 | B2 | 8/2011 | Hardin et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,241,226 | B2 | 8/2012 | Hibner et al. |
| 8,251,916 | B2 | 8/2012 | Speeg et al. |
| 8,371,443 | B2 | 2/2013 | Nock et al. |
| 8,454,531 | B2 | 6/2013 | Speeg et al. |
| 8,532,747 | B2 | 9/2013 | Nock et al. |
| 8,622,924 | B2 | 1/2014 | Speeg et al. |
| 8,702,623 | B2 | 4/2014 | Parihar et al. |
| 8,764,680 | B2 | 7/2014 | Rhad et al. |
| 8,801,742 | B2 | 8/2014 | Rhad et al. |
| 8,858,465 | B2 | 10/2014 | Fiebig |
| 8,938,285 | B2 | 1/2015 | Fiebig et al. |
| 9,095,326 | B2 | 8/2015 | Ritchie et al. |
| 9,326,755 | B2 | 5/2016 | Fiebig et al. |
| 9,345,457 | B2 | 5/2016 | Speeg et al. |
| 9,486,186 | B2 | 11/2016 | Fiebig et al. |
| 2006/0074345 | A1 | 4/2006 | Hibner |
| 2009/0131821 | A1 | 5/2009 | Speeg et al. |
| 2009/0192408 | A1* | 7/2009 | Mark ..................... A61B 90/39 600/562 |
| 2010/0152610 | A1 | 6/2010 | Parihar et al. |
| 2010/0160819 | A1 | 6/2010 | Parihar et al. |
| 2010/0160946 | A1* | 6/2010 | Mirizzi ............ A61B 17/12181 606/191 |
| 2012/0078086 | A1* | 3/2012 | Hoffa ................. A61B 10/0275 600/424 |
| 2012/0226146 | A1* | 9/2012 | Schwartz ............... A61B 90/98 600/424 |
| 2013/0041256 | A1* | 2/2013 | Fiebig ................... A61B 90/39 600/432 |
| 2013/0261438 | A1 | 10/2013 | Selis |
| 2013/0324882 | A1 | 12/2013 | Mescher |

OTHER PUBLICATIONS

Devicor Medical Products, Inc., "Mammotome," Site Map including Product list, downloaded Dec. 4, 2016, from http://www.mammotome.com/sitemap/, 2 pgs.

Hahn, M., et al., "Diagnostic Primer: Vacuum-Assisted Breast Biopsy with Mammotome®," Devicro Medical Germany GmBh, Nov. 11, 2012, Germany, Springer Medizin Verlag, copyright 2013, 130 pgs.

Hologic, Inc., "Breast biopsy markers for stereotactic," downloaded Dec. 6, 2016, from http://www.hologic.com/products/intervention-and-treatment/breast-biopsy/breast-biopsy-markers-stereotactic, 2 pgs.

International Search Report and Written Opinion dated Oct. 31, 2016 for Application No. PCT/US2016/044285, 16 pgs.

* cited by examiner

BIOPSY IMAGING ROD WITH AN EGRESS PORT, WITH A BIOPSY MARKER AND WITH A BIASED PUSHROD

This application is a National Stage Entry of PCT Ser. No. PCT/US16/44285, entitled "IMAGING ROD WITH ONBOARD MARKER FOR USE IN MRI BREAST BIOPSY PROCEDURES," filed Jul. 27, 2016, which claims priority to U.S. Ser. No. 62/198,491, entitled "IMAGING ROD WITH INTERNAL MARKER," filed Jul. 29, 2015, the disclosures of which are hereby incorporated by reference herein.

FIELD OF THE INVENTION

The disclosure relates to devices for use during a biopsy. In particular, the disclosure relates to imaging rods and markers for use in MRI breast biopsy procedures.

BACKGROUND OF THE INVENTION

Breast biopsy samples have been obtained in a variety of ways in various medical procedures including open and percutaneous methods using a variety of devices. For instance, some breast biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other breast biopsy devices may be fully or at least partially operable without being tethered or otherwise connected with another device.

The state of the art technology for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

During a breast biopsy procedure, various imaging techniques may be used to locate a biopsy site within the patient's body. Breast biopsy devices may be used under stereotactic guidance, ultrasound guidance, MRI guidance, Positron Emission Mammography ("PEM" guidance), Breast-Specific Gamma Imaging ("BSGI") guidance or otherwise. These imaging techniques may be used to identify features of interest within the patient's body, and also to position a biopsy needle for obtaining samples at the biopsy site.

"Vacuum-Assisted Breast Biopsy with Mammotome®", has an entire chapter, pp 78-107, discussing the steps in conducting a MRI-Guided Vacuum-Assisted Breast Biopsy with Mammotome MRI. This description also includes a list of the equipment required as well as showing images of patent undergoing this procedure.

In an MRI-guided breast biopsy procedure, after the patient is properly positioned on the table and a targeting device—either a grid and cubes combination or pillar, post and cradle support has been deployed and used, a baseline MRI image is taken to verify the target location. After that, a scalpel is used to incise the skin of the breast. Next an assembly, formed by an obturator disposed in a sleeve, is inserted through the incision to penetrate the breast tissue under the skin. In some acceptable surgical technique the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed. After the obturator or imaging rod has been removed, it is replaced in the sleeve with the needle of a breast biopsy probe. A cutter within the needle of the probe is used to remove tissue which is then conveyed either to a manual pick up location on the breast biopsy device, or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

The incision in the breast is closed using medically acceptable ways to close breaks in the skin.

Known breast biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326,755, entitled "Biopsy Device Tissue Sample Holder with Bulk Chamber and Pathology Chamber," issued on May 3, 2016. The disclosure of each of the above-cited U.S. patents is incorporated by reference herein.

Additional known breast biopsy devices and breast biopsy system components are disclosed in U.S. Pat. Pub. No. 2006/0074345, entitled "Biopsy Apparatus and Method," published Apr. 6, 2006 and now abandoned; U.S. Pat. Pub. No. 2008/0214955, entitled "Presentation of Biopsy Sample by Biopsy Device," published Sep. 4, 2008; U.S. Pat. Pub. No. 2009/0131821, entitled "Graphical User Interface For Biopsy System Control Module," published May 21, 2009, now abandoned; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0144188, entitled "Biopsy Device With Slide-In Probe," published Jun. 6, 2013; and U.S. Pat. Pub. No. 2013/0324882, entitled "Control for Biopsy Device," published Dec. 5, 2013. The disclosure of each of the above-cited U.S. patent application Publications, U.S. Non-Provisional patent applications, and U.S. Provisional patent applications is incorporated by reference herein.

A known localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

In U.S. Pat. No. 7,831,290, "MRI Biopsy Device Localization Fixture" issued Oct. 20, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Known Z-stop devices are disclosed in U.S. Pat. No. 7,507,210, entitled "Biopsy Cannula Adjustable Depth Stop," issued Mar. 24, 2009, the disclosure of which has been previously incorporated by reference herein.

It is typically desirable to mark a biopsy site so that the biopsy site may be identified in the future using an imaging technique, which may be different from an imaging technique used during the biopsy. A biopsy marker may be a small biocompatible object capable of being imaged using one or more imaging techniques. Biopsy markers are often enclosed in a bioabsorbable material (e.g., collagen) to help position the marker at the biopsy site.

Exemplary markers are commercially available and include, but are not limited to, the MAMMOMARK™, MICROMARK®, CORMARK™, HYDROMARK, and MAMMOSTAR brand marker devices available from Devicor Medical Products, Inc. of Cincinnati, Ohio, see http://www.mammotome.com/. Other commercially available marker devices are available from Hologic Inc. as SecureMark® and TriMark® biopsy site markers. See http://www.hologic.com/products/intervention-and-treatment/breast-biopsy/breast-biopsy-markers-stereotactic. Other commercially available marker devices are available from C.R. Bard Inc. as Gel Mark Ultra™, Gel Mark Ultra Cor™; SenoMark™; SenoMark Ultra™, SenoMark UltraCor™; SenoMark UltraCor MRI; StarchMark®; StarchMark® UltraCor; UltraClip™; UltraClip Dual Trigger™ and Ultra Cor™ biopsy site markers. See http://www.bardbiopsy.com/products/index_markers.php.

Accurate deployment of a biopsy marker to a biopsy site following a biopsy may present difficulties. A biopsy marker may be provided with a separate deployment device. Marker deployment devices typically include a flexible tube at the distal end. The flexible tube must be inserted through the biopsy needle.

Clinicians have reported that the deployment of the marker at the conclusion of an MRI Breast Biopsy is problematical, as commercially available deployment devices for markers typically include a long, flexible tube that must be aligned with the cannula opening.

It would be desirable to not have to use a long flexible tube to deploy a marker at the conclusion of a MRI Breast Biopsy procedure. It would also be desirable to not have to have three (3) separate sterile devices (the targeting set, the VABB device and the marker deployment device) be required for every MRI Breast Biopsy procedure.

While several systems and methods have been made and used for obtaining a breast biopsy sample, it is believed that no one prior to the inventor has made or used the invention described in the appended claims.

SUMMARY OF THE INVENTION

The following presents a broader description of one or more aspects in order to provide a basic understanding of such aspects. This description is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The first aspect of the instant claimed invention is a biopsy imaging rod, comprising: an elongated rod member having a sharp distal end and a channel extending from a proximal end to an egress port near the distal end; a biopsy marker positioned in the channel proximal to the egress port; and a pushrod slideably positioned in the channel adjacent to the biopsy marker extending from the proximal end of the elongated rod member to the egress port, the pushrod biased to bend toward the biopsy marker.

The second aspect of the instant claimed invention is a method of manufacturing a biopsy imaging rod having an onboard biopsy marker, the method comprising: molding an elongated rod member having a sharp distal end and a channel extending from a proximal end to ramp surface, the ramp surface extending to an egress port near the distal end; molding a pushrod sized to fit within the channel and extend from the proximal end of the elongated rod member to the egress port, the pushrod biased to bend; molding a marker holder sized to fit within the channel adjacent to the pushrod; positioning a biopsy marker at a distal end of the channel proximal to the ramp surface; inserting the marker holder into the channel from the proximal end of the elongated rod member; inserting the pushrod into the channel adjacent the marker holder such that the pushrod straightens as a distal end of the pushrod slides up the ramp surface.

A method of using a biopsy imaging rod including an onboard biopsy marker, to place a marker in a breast after a breast biopsy has been performed, said method comprising: inserting the biopsy imaging rod into a hollow biopsy needle such that an egress port of the biopsy imaging rod extends past a distal end of the biopsy needle; proximally retracting a pushrod located within the biopsy imaging rod relative to the biopsy imaging rod, the pushrod biased to bend toward the onboard biopsy marker after a distal end of the pushrod clears the onboard biopsy marker; and distally moving the pushrod relative to the biopsy imaging rod, the pushrod pushing the onboard biopsy marker along at least one ramped surface and out of the egress port with the result being that the marker is placed in the desired area within the breast.

The one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which.

A "Parts List" giving the number and name of each part shown in the Figures is included to guide the reader.

| Number | Part Name |
| --- | --- |
| 100 | Imaging Rod |
| 200 | Elongated Rod Member |
| 210 | Sharp Point |
| 212 | Imageable Portion |
| 212a | Sharp Point Faces |
| 214a | Sharp Point Edges |
| 220 | Egress Port |
| 230 | Internal Channel |
| 232 | Cavity |
| 234 | Elongated Portion |
| 236 | First Ramp Surface |
| 238 | Ledge |
| 240 | Second Ramp Surface |
| 300 | Pushrod |
| 310 | Elongated Portion |
| 312 | Distal End |
| 314 | Ramp Surface |
| 316 | Bent Portion |
| 320 | Handle Portion |
| 330 | Seal |
| 332 | Cavity |
| 336 | Ramp Surface |
| 338 | ledge |
| 340 | Second Ramp Surface |
| 400 | Biopsy Marker |
| 500 | Marker Holder |
| 510 | Elongated Portion |
| 512 | Ramp Surface |
| 514 | Flat Portion |
| 520 | Flange |
| 522 | Opening |

DETAILED DESCRIPTION OF THE INSTANT CLAIMED INVENTION

Various aspects are now described with reference to the drawings. In the following description, for purposes of explanation, numerous specific details are set forth in order to provide a thorough understanding of one or more aspects. It may be evident, however, that such aspects may be practiced without these specific details.

As stated previously, the first aspect of the instant claimed invention is a biopsy imaging rod, comprising: an elongated rod member having a sharp distal end and a channel extending from a proximal end to an egress port near the distal end; a biopsy marker positioned in the channel proximal to the egress port; and a pushrod slideably positioned in the channel adjacent to the biopsy marker extending from the proximal end of the elongated rod member to the egress port, the pushrod biased to bend toward the biopsy marker.

FIGS. 1A-1D illustrate an example of an imaging rod 100 according to an aspect of the present disclosure. The imaging rod 100 includes an elongated rod member 200, a pushrod 300, a biopsy marker 400, and a marker holder 500. The elongated rod member 200 may include a sharp point 210 at the distal end. As illustrated, the sharp point 210 includes 4 faces, but it should be apparent that the sharp point 210 may include fewer or more faces. The elongated rod member 200 further includes an egress port 220. The egress port 220 may be an opening into an interior channel of the elongated rod member 200. In an aspect, the egress port 220 may have a ramp surface. The egress port 220 may allow an onboard biopsy marker 400 stored in the channel to exit the elongated rod member 200, for example, when the elongated rod member 200 is positioned at a biopsy site. The marker holder 500 may seal the channel at a proximal end of the elongated rod member 200.

Figure 1A:
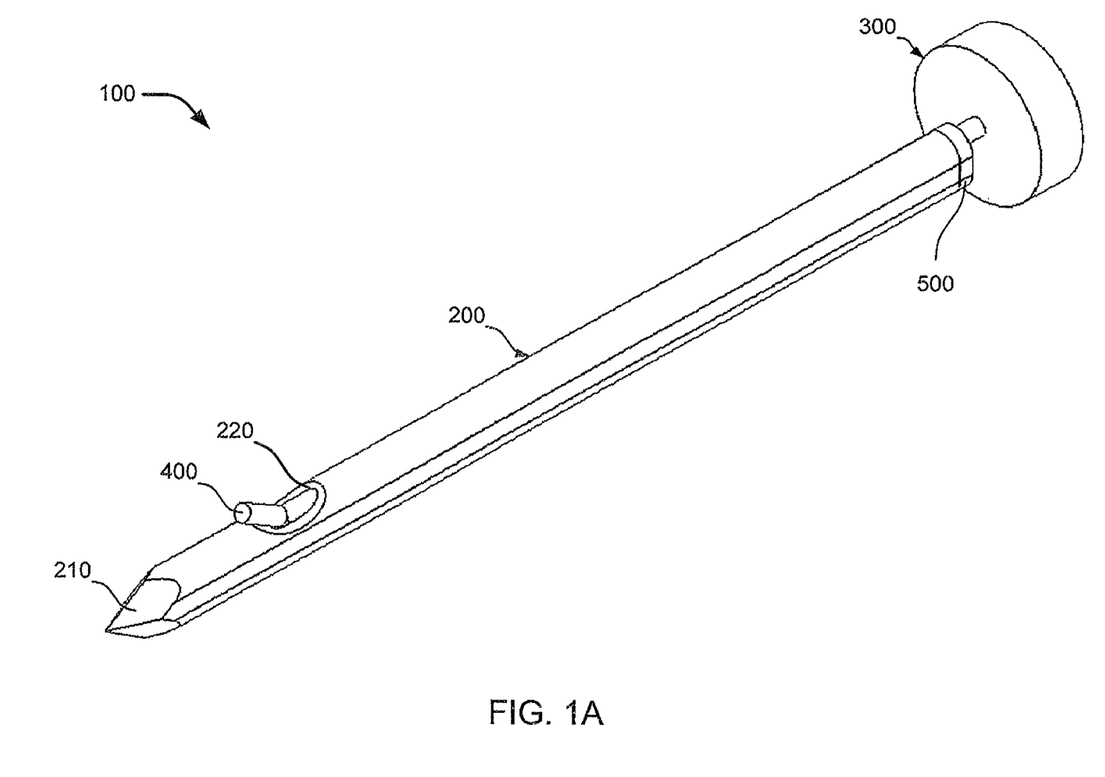
FIG. 1A is a perspective view of an example of an imaging rod according to an aspect of the present disclosure.
Figure 1B:
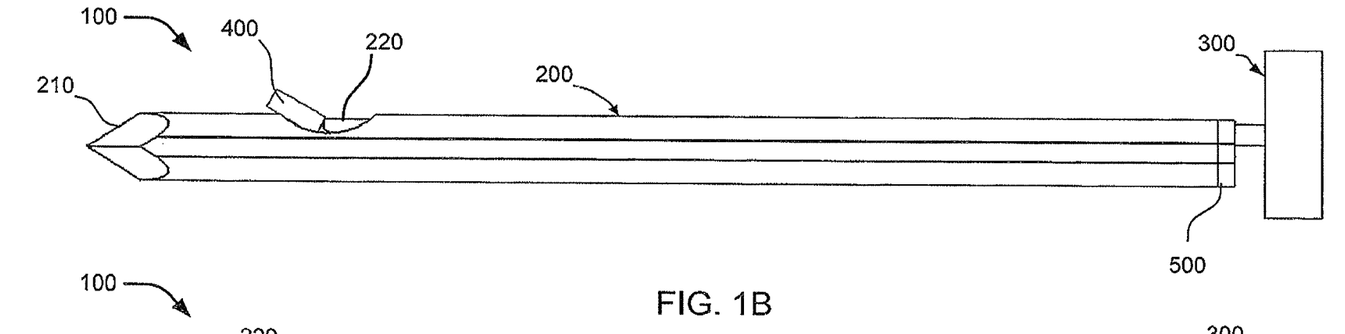
FIG. 1B is a side view of an example of an imaging rod according to an aspect of the present disclosure.
Figures 1C, 1D:
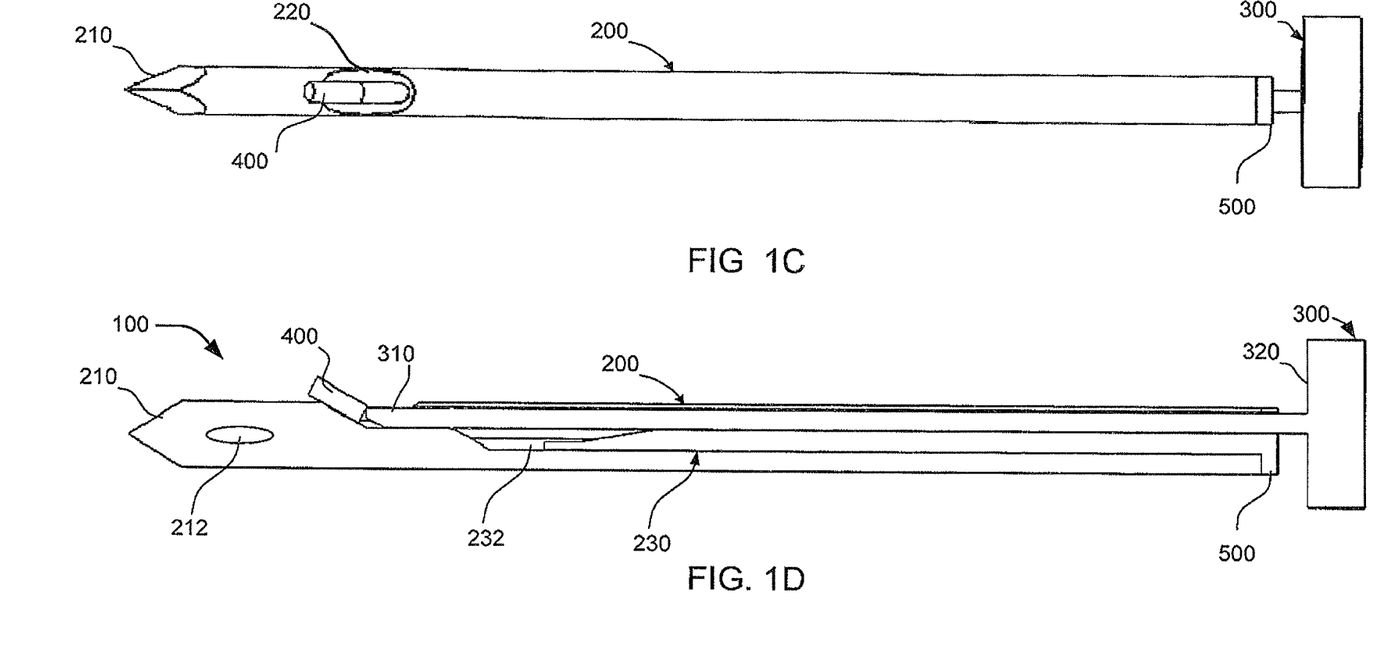
FIG. 1C is a top view of an example of an imaging rod according to an aspect of the present disclosure.
FIG. 1D is a cross-sectional side view of an example of an imaging rod according to an aspect of the present disclosure.

As illustrated in FIG. 1D, an internal channel 230 may extend from a proximal end of the elongated rod member 200 to the egress port 220 (shown in FIGS. 1A, 1B and 1C). The pushrod 300 may include an elongated portion 310 and a handle portion 320. The handle portion 320 may be located at the proximal end of the elongated rod member 200. The elongated portion 310 may extend through the channel 230 from the proximal end of the elongated rod member 200 to the egress port 220. The marker holder 500 may also extend from the proximal end of the elongated rod member 200 toward the egress port 220. The marker holder 500 may be shorter than the pushrod 300 such that a cavity 232 of the channel provides a space for the biopsy marker 400 in an initial configuration.

The elongated rod member 200 may further include an imageable portion 212. The imageable portion 212 may be imageable using a first imaging technology, for example, magnetic resonance (MR). As used herein, the term "imageable" means the characteristic of being visible in an image generated using an imaging technology. In an aspect, the imageable portion 212 may include an imageable object molded into the distal end of the elongated rod member 200. In another aspect, the imageable portion 212 may be formed due to the properties of the material used to form the elongated rod member 200 or the imageable portion 212. For example, the imageable portion 212 may be formed using a plastic mixed with an imageable dye or powder.

The marker 400 may be any biopsy marker sized to fit within the cavity 232 and exit via the egress port 220. For example, the marker 400 may be a biopsy marker marketed under the MAMMOTOME®, HYDROMARK®, MAMMOMARK®, or MAMMOSTAR® names or another marker known in the art. In an aspect, the marker 400 may be generally cylindrical. The marker 400 may include an imageable element and a bioabsorbable casing (e.g., collagen). The imageable element may, for example, be imageable under one or more of stereotactic, ultrasound, or MRI analysis. In an aspect, the imageable element may be imageable using a different imaging technology than an imaging technology under which the imageable portion 212 is imageable. For example, the imageable portion 212 may be imageable under MRI, whereas the imageable element of marker 400 may be imageable under stereotactic. The imageable element may have a distinct shape that may differentiate the marker 400 from natural anatomic features as well as other markers used for previous biopsies.

Figure 2A:
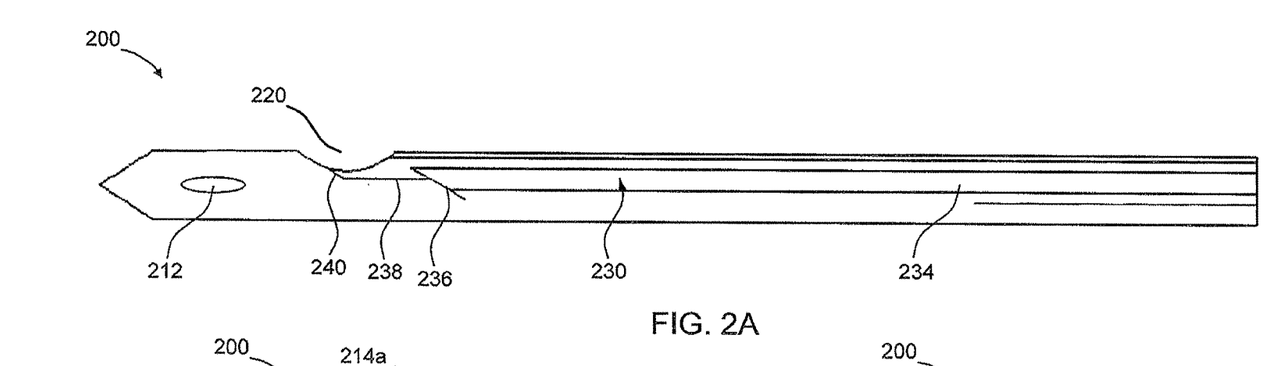
FIG. 2A is a cross-sectional side view of an example elongated rod member according to an aspect of the present disclosure.

FIG. 2A illustrates a cross-sectional side view of the elongated rod member 200. The channel 230 may include an elongated portion 234 extending from the proximal end of the elongated rod member 200. The elongated portion 234 may have an elliptical or oval cross-section (see FIG. 2C) normal to the longitudinal axis. In an aspect, the elongated portion 234 may be off center within the elongated rod member 200 such that a wall adjacent the egress port 220 is thinner than an opposite wall. The off center position of the channel 230 may provide for a shorter distance for the marker 400 to travel, while also providing rigidity and strength to the elongated rod member 200. The channel 230 may be further defined by a first ramp surface 236 at a distal end of the channel 230. The first ramp surface 236 may form a distal boundary of the cavity 232.

As discussed in further detail below, the marker holder 500 or ramp surface 512 thereof may form a proximal boundary of the cavity 232. In an initial configuration, the marker 400 may be located in the cavity 232 adjacent the first ramp surface 236. In an aspect, the cavity 232 may be open to the channel 230 such that the marker 400 may contact the pushrod 300. In another aspect, a flexible flap may initially separate the marker 400 from the pushrod 300. The first ramp surface may extend from the elongated portion 234 to a ledge 238. The ledge 238 may be a longitudinal flat surface. In the initial configuration, a distal end of the pushrod 300 may be adjacent the ledge 238. The ledge 238 may maintain the pushrod 300 in a straight configuration when the imaging rod 100 is in the initial configuration. The ledge 238 may extend from the first ramp surface 236 to a second ramp surface 240. The second ramp surface 240 may extend from the ledge 238 to the egress port 220. The second ramp surface 240 may move the marker 400 radially toward the egress port 220 as the pushrod 300 moves the marker 400 distally. Accordingly, the second ramp surface 240 may eject the marker 400 from the elongated rod member 200 via the egress port 220.

Figure 2B:
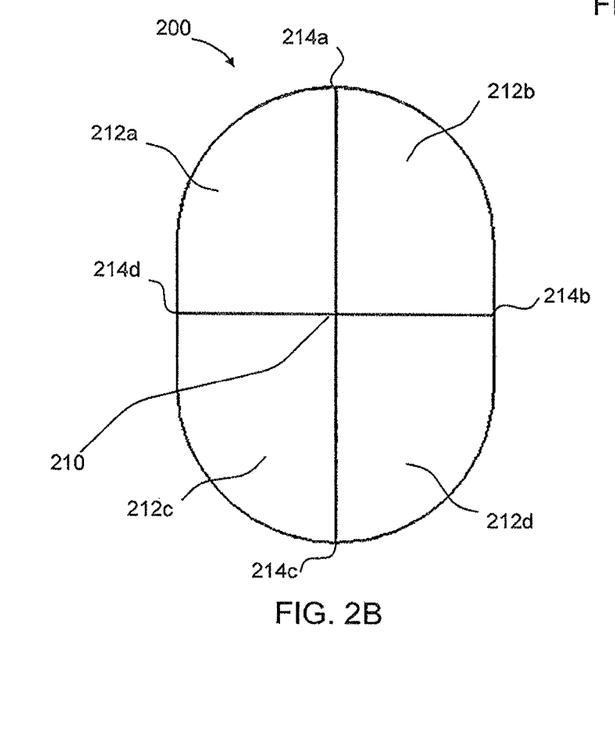
FIG. 2B is a distal end view of an example elongated rod member according to an aspect of the present disclosure.

As illustrated in FIG. 2B, the distal end of the elongated rod member 200 may include a sharp point 210. In an aspect, the sharp point 210 may be formed by the intersection of multiple faces 212a-d along edges 214a-d. In an aspect, the faces 212a-d may be concave.

Figure 2C:
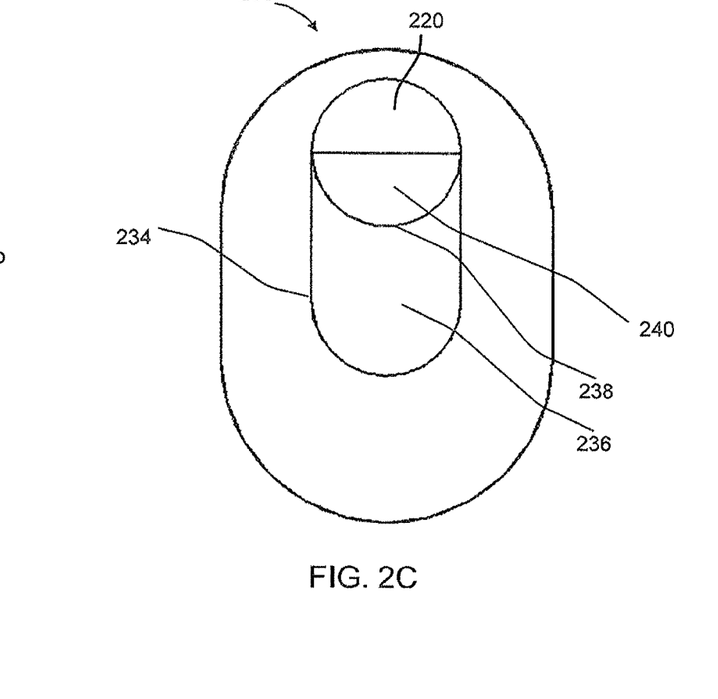
FIG. 2C is a proximal end view of an example elongated rod member according to an aspect of the present disclosure.

As illustrated in FIG. 2C, the elongated portion 234 of the channel 230 may open at the proximal end of the elongated rod member 200. The elongated portion 234 may have, for example, an elliptical or oval cross-section. The first ramp surface 236 may extend from one side (illustrated as the bottom) of the channel 230 opposite the egress port 220 to the ledge 238. The second ramp surface 240 may extend from the ledge 238 to the egress port 220, which may also include a ramp surface. In another aspect, a single ramp surface may extend from the side opposite the egress port 220 to the egress port 220. Other combinations of ramp surfaces and/or ledges may also be used.

Figure 3:
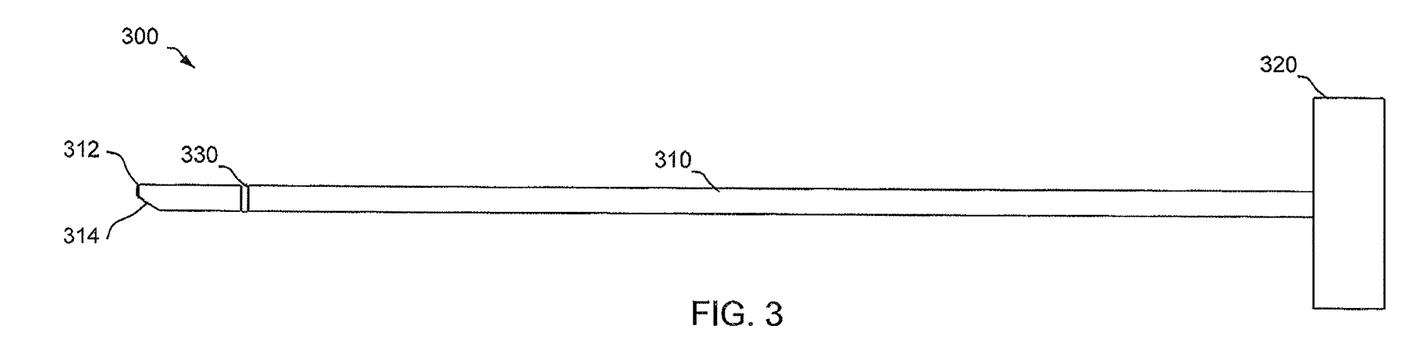
FIG. 3 illustrates an example pushrod in a straight configuration according to an aspect of the present disclosure.

FIG. 3 illustrates an example pushrod 300 in a straight configuration. The pushrod 300 may include an elongated portion 310 and a handle portion 320. The elongated portion 310 may extend from the handle portion 320 to a distal end 312. The distal end 312 may contact the marker 400 to move the marker 400 distally. A ramp surface 314 may be located adjacent the distal end 312. The ramp surface 314 may slide along the inner surfaces (e.g., cavity 332, ramp surface 336, ledge 338) of elongated rod member 200.

In an aspect, the pushrod 300 may include a seal 330. The seal 330 may prevent fluid from entering the elongated rod member 200 when the imaging rod 100 is in the initial configuration. For example, the seal 330 may contact the inner surfaces of the elongated rod member 200 at a narrow point of the channel 230 at the ledge 338. In an aspect, the seal 330 may be, for example, an O-ring surrounding the elongated portion 310. The elongated portion 310 may include a groove or similar feature for retaining the O-ring. In another aspect, the seal 330 may be integrally formed with the elongated portion 310.

Figure 4:
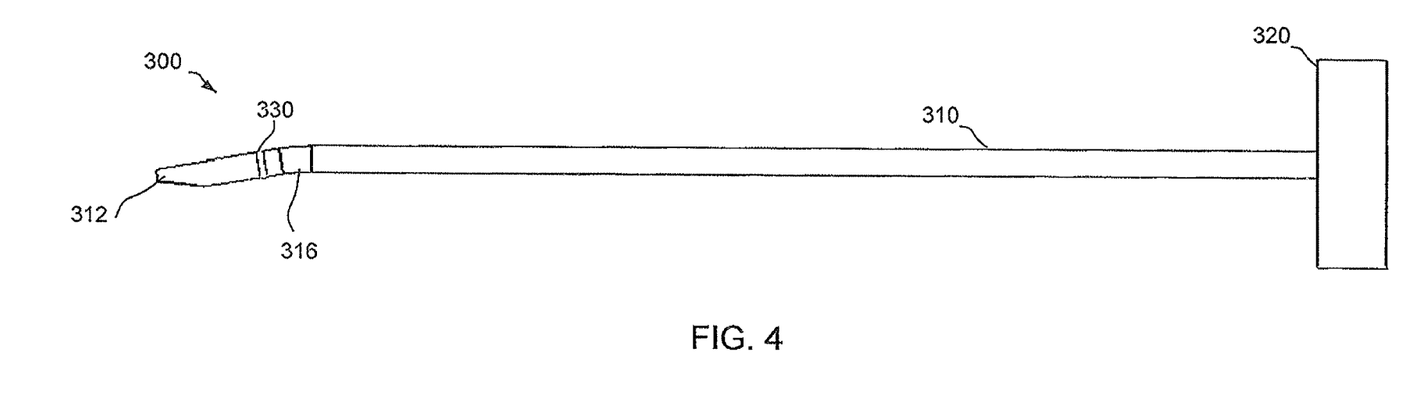
FIG. 4 illustrates an example pushrod in a curved configuration according to an aspect of the present disclosure.

FIG. 4 illustrates an example pushrod 300 in a curved configuration according to an aspect of the present disclosure. The pushrod 300 may be molded such that the pushrod 300 is biased toward the curved configuration. In the curved configuration, the pushrod 300 may be bent, for example, the pushrod 300 may include a bent portion 316 proximal to the seal 330. In an aspect, the bent portion 316 may be along a portion of the pushrod 300 adjacent the cavity 232 when the imaging rod 100 is in the initial configuration. The bent portion 316 may cause the distal end 312 to enter the cavity 232 when the pushrod 300 is retracted proximally such that the distal end 312 clears the marker 400 in the cavity 232.

Figure 5A:
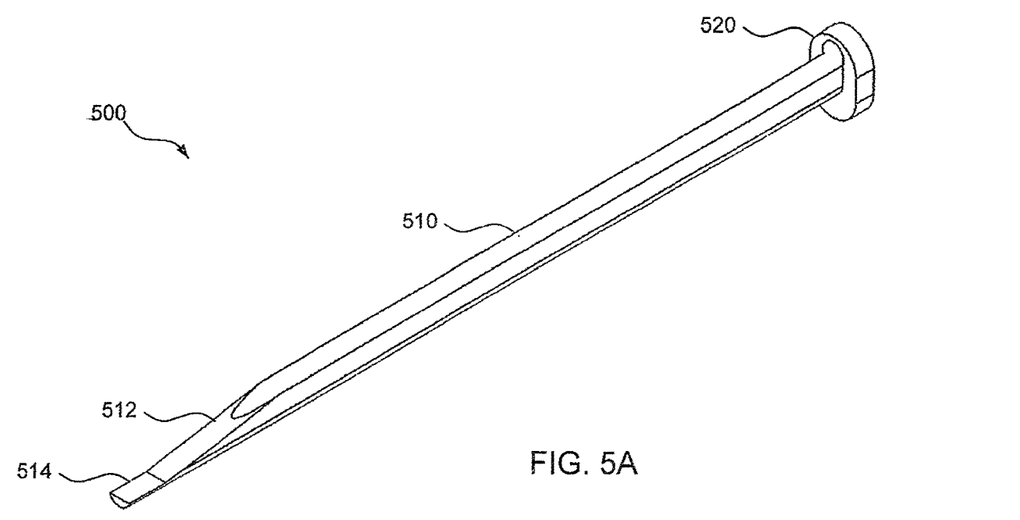
FIG. 5A illustrates a perspective view of an example marker holder according to an aspect of the present disclosure.
Figure 5B:
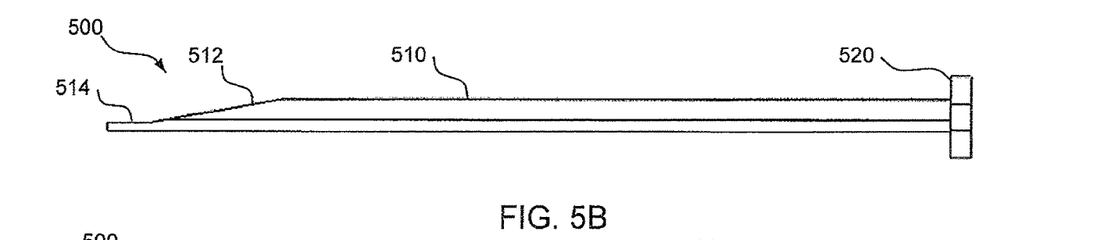
FIG. 5B illustrates a side view of an example marker holder according to an aspect of the present disclosure.

In an aspect, a distance from the distal end 312 to the bent portion 316 may be approximately equal to a length of the ramp surface 512 (FIG. 5B). In an aspect, the pushrod 300 may include an internal element to selectively place the pushrod 300 in the straight configuration (FIG. 3). For example, the pushrod 300 may include an internal channel that accepts a straight rod. The straight rod may be pushed through the bent portion 316 to cause the pushrod 300 to straighten. The pushrod 300 may be placed in the straight configuration during assembly, and then the straight rod may be retracted or removed to bias the pushrod 300 toward the curved configuration (FIG. 4).

In an aspect, the pushrod 300 may include a locking feature that engages the pushrod 300 with the elongated rod member 200 and/or the marker holder 500. The locking feature may prevent the pushrod 300 from being unintentionally retracted proximally, for example, when removing the imaging rod 100 from a biopsy needle. The locking feature may include, for example, internal or external threads, one or more corresponding flanges and grooves, retractable tabs, a fastener, etc.

Figure 5C:
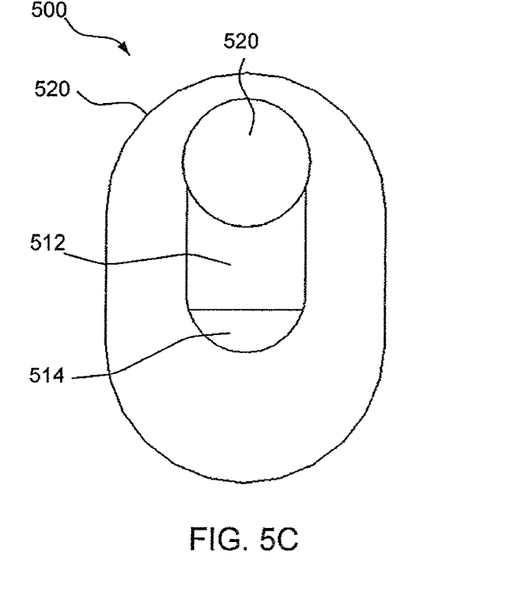
FIG. 5C illustrates a distal end view of an example marker holder according to an aspect of the present disclosure.

FIGS. 5A-5C illustrate an example marker holder 500 according to an aspect of the present disclosure. The marker holder 500 may seal the proximal end of the elongated rod member 200, retain the marker 400 in the cavity 232, and retain the pushrod 300 in an initial straight configuration. In an aspect, the marker holder 500 may include an elongated portion 510 and a proximal flange 520. The elongated portion 510 may extend longitudinally within the channel 230. In an aspect, a surface of the elongated portion 510 that contacts the pushrod 300 may be shaped to correspond to the surface of the pushrod 300. For example, as illustrated, the elongated portion 510 may have a curved groove that corresponds to a rounded surface of the pushrod 300. The elongated portion 510 may include a ramp surface 512. The ramp surface 512 may define a proximal boundary of the cavity 232. The ramp surface 314 of the pushrod 300 may contact the ramp surface 512 when the pushrod 300 is retracted proximally. The elongated portion 510 may further include a flat portion 514. The flat portion 514 may form a distal end of the marker holder 500. The flat portion 514 may contact the marker 400 and prevent the marker 400 from moving proximally up the ramp surface 512.

The proximal flange 520 may seal a proximal end of the channel 230. In an aspect, the proximal flange 520 may abut a proximal surface of the elongated rod member 200. In another aspect, an outer surface of the proximal flange 520 may seal against an inner surface of the elongated rod member 200. The proximal flange 520 may include an opening 522. The opening 522 may be a hole through the proximal flange 520. The pushrod 300 may pass through the opening 522.

Figure 5D:
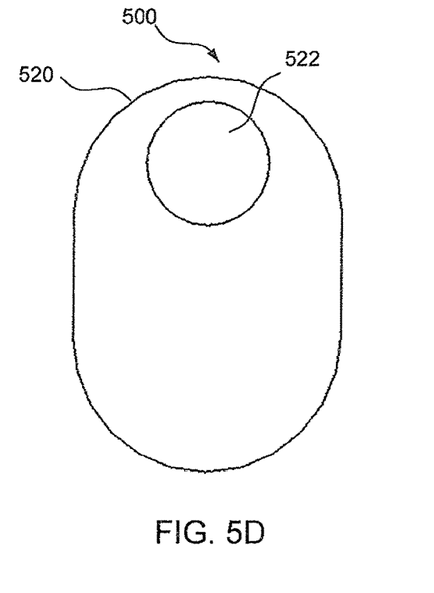
FIG. 5D illustrates a proximal end view of an example marker holder according to an aspect of the present disclosure.

In an aspect, the opening 522 may be a keyway for controlling the movement of the pushrod 300. The keyway may have a shape that prevents the pushrod 300 from freely rotating. For example, the keyway may be rectangular or include one or more slots or projections in a perimeter of the keyway. The keyway may ensure that the pushrod 300 remains in an orientation such that the bend will bias the distal end 312 into the cavity 232. In an aspect, the keyway may also cause the pushrod 300 to rotate at various longitudinal positions. For example, the pushrod 300 may include a corresponding slot or projection along a portion of the elongated portion 310 that causes the pushrod to rotate when passing through the keyway.

Figure 6A:
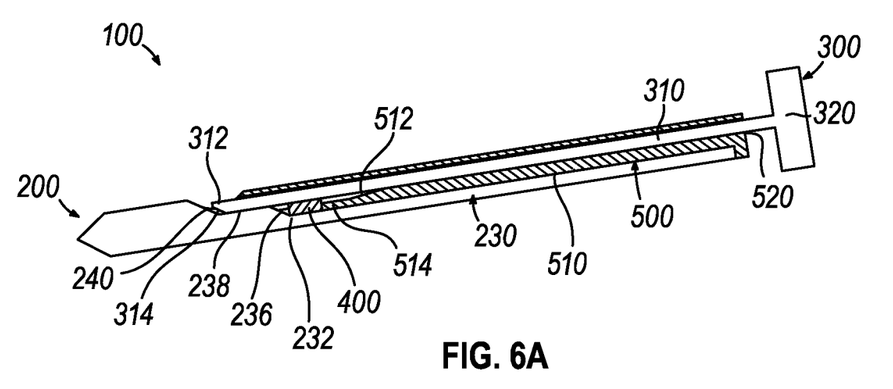
FIG. 6A illustrates a cross-sectional side view of an example imaging rod in an initial configuration according to an aspect of the present disclosure.

FIG. 6A illustrates a cross-sectional side view of the imaging rod 100 in an initial configuration according to an aspect of the present disclosure. The imaging rod 100 may be placed in the initial configuration during manufacturing. In the initial configuration, the pushrod 300 may be in a straight configuration with the distal end 312 and ramp surface 314 contacting the second ramp surface 340. The ledge 338 may prevent the pushrod 300 from bending to the curved configuration. The marker 400 may be positioned in the cavity 232 distal to the marker holder 500 and adjacent the pushrod 300. The imaging rod 100 may be moved to a retracted configuration by moving the pushrod 300 proximally, for example, by pulling on the handle portion 320.

Figure 6B:
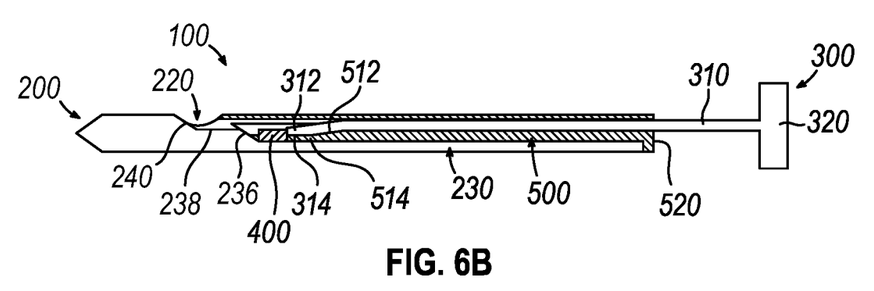
FIG. 6B illustrates a cross-sectional side view of an example imaging rod in a retracted configuration according to an aspect of the present disclosure.

FIG. 6B illustrates a cross-sectional side view of the imaging rod 100 in a retracted configuration according to an aspect of the present disclosure. The pushrod 300 may assume the curved configuration as the distal end 312 clears the marker 400. The distal end 312 may move into the cavity 232 adjacent to the flat portion 514 of the marker holder. In the retracted configuration, the seal 330 no longer seals the channel 230, and fluid (e.g., blood) may enter the channel 230.

Figure 6C:
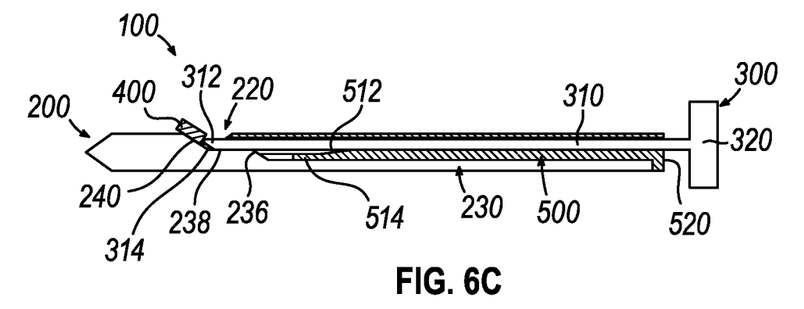
FIG. 6C illustrates a cross-sectional side view of an example imaging rod in a deployed configuration according to an aspect of the present disclosure.

FIG. 6C illustrates a cross-sectional side view of the imaging rod 100 in a deployed configuration according to an aspect of the present disclosure. The imaging rod 100 may be placed into the deployed configuration from the retracted configuration by moving the pushrod 300 distally, for example, by pushing on the handle portion 320. As the pushrod 300 moves distally, the distal end 312 may slide along the ramp surface 512 and the flat portion 514 to contact the marker 400. The distal end 312 may then push the marker 400 up the first ramp surface 336, across the ledge 338, up the second ramp surface 340, and out the egress port 220. Accordingly, the marker 400 may be deployed to a biopsy site adjacent the egress port 220 to mark the site of the biopsy. In an aspect, the imaging rod 100 may be disposed after deploying the marker 400.

The second aspect of the instant claimed invention is a method of manufacturing a biopsy imaging rod having an onboard biopsy marker, the method comprising: molding an elongated rod member having a sharp distal end and a channel extending from a proximal end to ramp surface, the ramp surface extending to an egress port near the distal end; molding a pushrod sized to fit within the channel and extend from the proximal end of the elongated rod member to the egress port, the pushrod biased to bend; molding a marker holder sized to fit within the channel adjacent to the pushrod; positioning a biopsy marker at a distal end of the channel proximal to the ramp surface; inserting the marker holder into the channel from the proximal end of the elongated rod member; inserting the pushrod into the channel adjacent the marker holder such that the pushrod straightens as a distal end of the pushrod slides up the ramp surface.

Further to the description of the method, the method may include forming an elongated rod member having a sharp distal end and a channel extending from a proximal end to ramp surface, the ramp surface extending to an egress port near the distal end. In an aspect, for example, the elongated rod member may be the example elongated rod member 200. In an aspect, the elongated rod member 200 may be molded from a biocompatible plastic in one piece or multiple pieces that are then joined together. In an aspect, the elongated rod member 200 may be molded around the imageable portion 212. In another aspect, the elongated rod member 200 may be formed via 3D printing.

The method of the second aspect of the instant claimed invention may include forming a pushrod sized to fit within the channel and extend from the proximal end of the elongated rod member to the egress port, the pushrod biased to bend. In an aspect, for example, the pushrod may be the example pushrod 300. In an aspect, the pushrod 300 may be molded from a biocompatible plastic. In an aspect, the pushrod 300 may be a single molded piece. In another aspect, the pushrod 300 may be molded as a separate elongated portion 310 and handle portion 320. The handle portion 320 may be jointed to the elongated portion 310 such that the handle portion 320 may rotate, for example, to engage or disengage a locking feature. The pushrod 300 may be molded in the bent configuration. The flexibility of the biocompatible plastic may allow the pushrod 300 to be forced into the straight configuration (FIG. 3) while being biased toward the curved configuration (FIG. 4). The pushrod 300 may also be formed via 3D printing.

The method may include forming a marker holder sized to fit within the channel adjacent to the pushrod. In an aspect, for example, the marker holder may be the example marker holder 500. In an aspect, the marker holder 500 may be molded from a biocompatible plastic. The marker holder 500 may be a single molded piece. The marker holder 500 may also be formed via 3D printing.

The method may include positioning a biopsy marker at a distal end of the channel proximal to the ramp surface. The biopsy marker may be any biopsy marker sized to fit within the cavity 232 and exit through the egress port 220. The biopsy marker may be inserted via either the egress port 220 or the proximal opening of the channel 230.

The method may include inserting the marker holder 500 into the channel 230 from the proximal end of the elongated rod. In an aspect, the marker holder 500 may have a feature (e.g., teeth) that engages a surface of the elongated rod member 200 upon insertion. In another aspect, an adhesive or solvent welding may permanently join the marker holder 500 to the elongated rod member 200. In yet another aspect, the marker holder 500 may be integrally formed with the elongated rod member 200, making this step of the method optional.

The method may further optionally include covering the biopsy marker with a tool inserted through the egress port. The tool may include a thin blade that covers the biopsy marker 400. The tool may extend from the egress port 220 to the ramp surface 512. The tool may be flexible such that the tool bends as the pushrod 300 is inserted.

The method may include inserting the pushrod into the channel adjacent the marker holder such that the pushrod straightens as a distal end of the pushrod slides up the ramp surface. In an aspect, the pushrod 300 may be inserted through the opening 522. The pushrod 300 may be forced into a straight configuration as the bent portion 316 travels through the elongated portion 234 adjacent the elongated portion 510. When the distal end 312 of the pushrod 300 reaches the ramp surface 512, the pushrod may bend. In an aspect, the tool may prevent the pushrod from moving the marker 400. In another aspect, the pushrod 300 may be rotated as the distal end 312 passes through the cavity 232 such that the pushrod does not return to the curved configuration. In yet another aspect, the pushrod 300 may be straightened using an internal straightening feature as the pushrod is inserted into the channel.

The method may conclude by removing the tool after inserting the pushrod into the channel. The tool may be removed by pulling the tool distally through the egress port 220.

A method of using a biopsy imaging rod including an onboard biopsy marker, to place a marker in a breast after a breast biopsy has been performed, said method comprising: inserting the biopsy imaging rod into a hollow biopsy needle such that an egress port of the biopsy imaging rod extends past a distal end of the biopsy needle; proximally retracting a pushrod located within the biopsy imaging rod relative to the biopsy imaging rod, the pushrod biased to bend toward the onboard biopsy marker after a distal end of the pushrod clears the onboard biopsy marker; and distally moving the pushrod relative to the biopsy imaging rod, the pushrod pushing the onboard biopsy marker along at least one ramped surface and out of the egress port with the result being that the marker is placed in the desired area within the breast.

The method of the third aspect of the instant claimed invention may include inserting the imaging rod into a hollow biopsy needle such that an egress port of the imaging rod extends past a distal end of the biopsy needle. In an aspect, for example, the imaging rod 100 may be inserted into a biopsy needle. In an aspect, the imaging rod 100 may be inserted into the biopsy needle before the biopsy needle is inserted into a patient. In another aspect, the imaging rod 100 may be inserted into the biopsy needle during a biopsy procedure while the biopsy needle is located within a patient. In an aspect, the imaging rod may be inserted until a feature of the imaging rod (e.g., flange 520) abuts a proximal end of the biopsy needle.

The method of the third aspect may optionally include imaging the imaging rod 100 using a first imaging technology. In an aspect, for example, the imaging rod 100 may be imaged using MRI. The MRI imaging may be used to determine whether the imaging rod 100 and biopsy needle are in a correct position. For example, an MRI image may indicate whether the imaging rod is located within or adjacent to a lesion, tumor, or biopsy site.

The method may include proximally retracting the pushrod 300 located within the biopsy imaging rod relative to the biopsy imaging rod. In an aspect, for example, the pushrod may be the pushrod 300. The pushrod 300 may be biased to bend toward the onboard biopsy marker after a distal end 312 of the pushrod 300 clears the onboard biopsy marker 400. The pushrod 300 may be proximally retracted by, for example, pulling on the handle portion 320. A locking feature may be disengaged before retracting the pushrod 300. The flange 520 may be held while proximally retracting the pushrod 300 to prevent movement of the imaging rod 100. The pushrod 300 may be proximally retracted until the distal end of the pushrod 300 clears the onboard biopsy marker. In an aspect, the pushrod 300 may include markings or another indication of when the pushrod 300 has been sufficiently retracted. The pushrod 300 may also include a stop or other limiting feature to prevent excessive proximal movement of the pushrod 300.

The method of the third aspect may include distally moving the pushrod relative to the imaging rod. The pushrod 300 may push the onboard biopsy marker 400 along at least one ramped surface and out of the egress port. In an aspect, the pushrod 300 may be distally moved by pushing on the handle portion 320. The flange 520 and/or the biopsy needle may be held to prevent the imaging rod 100 from being further inserted. When the biopsy marker 400 is pushed out of the egress port 220, the biopsy marker 400 may remain at a biopsy site to mark the biopsy site.

The method of the third aspect may optionally include imaging the biopsy marker 400 using a second imaging technology. In an aspect, the second imaging technology may be the same or different than the first imaging technology. For example, the biopsy marker 400 may be imaged using MRI or stereotactic or ultrasound after the biopsy is completed.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. A biopsy imaging rod, comprising:
   an elongated rod member having a sharp distal end and a channel extending from a proximal end to an egress port near the distal end;
   a biopsy marker positioned in the channel proximal to the egress port;
   a marker holder. the marker holder and the elongated rod member together defining a pushrod lumen; and
   a pushrod slideably positioned in the pushrod lumen adjacent to the biopsy marker extending from the proximal end of the elongated rod member to the egress port, the pushrod having a bent portion, the bent portion being biased such that the bent portion is configured to bend a distal end of the pushrod toward the biopsy marker.

2. The biopsy imaging rod of claim 1, the elongated rod member further comprising an imageable portion between the distal end of the elongated rod member and the egress port.

3. The biopsy imaging rod of claim 1, the marker holder being positioned in the channel proximal to the biopsy marker and adjacent the pushrod.

4. The biopsy imaging rod of claim 1, the elongated rod member including a ramp surface at a distal end of the channel.

5. The biopsy imaging rod of claim 4, the ramp surface extending to the egress port.

6. A method of using a biopsy imaging rod including an onboard biopsy marker, to place the onboard biopsy marker in a breast after a breast biopsy has been performed, said method comprising:
   (a) inserting the biopsy imaging rod into a hollow biopsy needle such that an egress port of the biopsy imaging rod extends past a distal portion of the biopsy needle;
   (b) proximally retracting a pushrod located within the biopsy imaging rod relative to the biopsy imaging rod, the pushrod having a bent portion being resiliently biased to bend a distal end of the pushrod toward the onboard biopsy marker after the distal end of the pushrod clears a proximal end of the onboard biopsy marker; and
   (c) distally moving the pushrod relative to the biopsy imaging rod, the pushrod pushing the onboard biopsy marker along at least one ramped surface and out of the egress port with the result being that the onboard biopsy marker is placed in a desired area within the breast.

7. The method of claim 6, further comprising imaging the biopsy imaging rod to identify the position of an imageable portion of the biopsy imaging rod relative to the biopsy needle.

8. The method of claim 6, the step of proximally retracting the pushrod including proximally retracting the pushrod relative to a marker holder such that the bent portion of the pushrod bends the distal end of the pushrod into a cavity at least partially defined by the marker holder.

9. The method of claim 6, the step of proximally retracting the pushrod. including proximally retracting the pushrod relative to a marker holder such that the bent portion of the pushrod bends the distal end of the pushrod toward a ramp defined by the marker holder.

10. The method of claim 9, the step of distally moving the pushrod including pushing the distal tip along the ramp defined by the marker holder and into contact with the onboard biopsy marker.

11. A biopsy imaging rod, comprising:
   (a) an elongated rod member having a distal tip and an egress port proximate the distal tip, the elongated rod member defining an elongated channel extending from an open proximal end of the elongated rod member to the egress port;
   (b) a marker holder disposed within the elongated channel of the elongated rod member, the elongated rod member and the marker holder together defining a cavity for holding a biopsy site marker in an initial position within the elongated rod member; and
   (c) a pushrod disposed within the elongated channel of the elongated rod member proximate the marker holder, the pushrod being configured to move within the elongated channel, the pushrod having a distal tip and a bent portion proximate the distal tip, the bent portion having a resilient bias configured to bend the distal tip of the pushrod toward the cavity defined by the marker holder upon movement of the pushrod relative to the marker holder.

12. The biopsy imaging rod of claim 11, the marker holder having a first ramp, the first ramp at least partially defining the cavity for holding the biopsy site marker.

13. The biopsy imaging rod of claim 12, the elongated rod member further having a second ramp, the second ramp being proximate the cavity, the second ramp being configured to project the biopsy site marker away from the cavity toward the egress port.

14. The biopsy imaging rod of claim 13, the elongated rod member further having a third ramp, the third ramp being proximate the egress port, the third ramp being configured to eject the biopsy site marker though the egress port.

15. The biopsy imaging rod of claim 12, the bent portion being further configured to bend the distal tip of the pushrod toward the cavity defined by the marker holder and into contact with the first ramp upon movement of the pushrod relative to the marker holder.

16. The biopsy imaging rod of claim 11, the marker holder being removably disposed within the elongated channel of the elongated rod member.

17. The biopsy imaging rod of claim 11, the marker holder having an engagement feature configured to engage the elongated rod member and hold the marker holder within the elongated rod member.

18. The biopsy imaging rod of claim 17, the engagement feature including one or more teeth.

\* \* \* \* \*